United States Patent [19]

Rephaeli et al.

[11] Patent Number: 5,569,675
[45] Date of Patent: Oct. 29, 1996

[54] METHODS OF USING CARBOXYLIC ACID ESTERS TO INCREASE FETAL-HEMOGLOBIN LEVELS

[75] Inventors: Ada Rephaeli, Palo Alto, Calif.; Abraham Nudelman, Rehovot; Matityahu Shaklai, Tel Aviv, both of Israel

[73] Assignees: Bar Ilan University, Ramat Gan; Mor Research Applications Ltd., Givat Shmuel, both of Israel

[21] Appl. No.: 206,690

[22] Filed: Mar. 7, 1994

[51] Int. Cl.[6] .................................... A61K 31/225
[52] U.S. Cl. ..................... 514/547; 514/512; 514/533; 514/548; 514/815; 514/895
[58] Field of Search .................... 560/263; 514/512, 514/547, 548, 533, 895, 815

[56] References Cited

U.S. PATENT DOCUMENTS

| | | | |
|---|---|---|---|
| 4,822,821 | 4/1989 | Perrine | 514/557 |
| 5,025,029 | 6/1991 | Perrine | 514/381 |
| 5,200,553 | 4/1993 | Nudelman et al. | 560/263 |
| 5,216,004 | 6/1993 | Perrine | 514/381 |

OTHER PUBLICATIONS

Charache et al., 1993, PNAS, 80:4842–4846 *Treatment of sickel cell anemia with 5–azacytidine results in increased fetal hemoglobin production and is associated with nonrandom hypomethylation of DNA around the μ–δ–βglobin gene complex.*

Charache et al., 1987, Blood, 69:109–116 *Hydroxyurea–Induced Augmentation of Fetal Hemoglobin Production in Patients with Sickle Cell Anemia.*

Perrine and Faller, 1993, Experiencia, 49:133–137 *Butyrate–induced reactivation of the fetal globin genes: A molecular treatment for the β–hemoglobinopathies.*

Dover et al., 1992, New Eng. J. Med., 327:569–570 *Increased Fetal Hemoglobin in Patients Receiving Sodium 4–Phenylbutyrate.*

Fibach et al., 1993, Blood, 82:1–7 *Enhanced Fetal Hemoglobin Production by Phenylacetate and 4–Phenylbutyrate in Erythroid Precursors Derived From Normal Donors and Patients with Sickle Cell Anemia and β–Thalassemia.*

*Primary Examiner*—Shailendra Kumar
*Attorney, Agent, or Firm*—Pennie & Edmonds

[57] ABSTRACT

This invention relates to novel methods of increasing the level of fetal hemoglobin (HbF) in a subject and methods of treating, preventing or ameliorating β-globin or other HbF-related disorders by increasing the level of HbF in a subject in need of such treatment comprising administering one or more compounds of the Formulae (I), (II), or (III):

(I) $XCH_2$—CHX—CHX—C(=O)—O—Z
(II) $CH_3$—CO—$CH_2$—C(=O)—O—Z
(III) $CH_3$—$CH_2$—CO—C(=O)—O—Z wherein:

X is H, or one of X only may be OH;
Z is —CHR—O—C(=O)R', —CHR—O—C(=O)—O—R', or

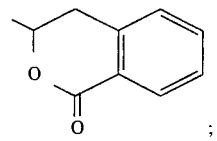

;

R is H, alkyl, aryl, arylalkyl; and
R' is alkyl, aminoalkyl, aralkyl, aryl, alkoxy, aralkoxy and aryloxy, in which aryl by itself, and aryl in aralkyl, aralkoxy and aryloxy are each selected from the group consisting of phenyl, naphthyl, furyl, or thienyl, each of which is unsubstituted or substituted by at least one substituent selected from the group consisting of alkyl, alkoxy, or halogen; and pharmaceutically acceptable salts and prodrugs thereof.

22 Claims, No Drawings

METHODS OF USING CARBOXYLIC ACID ESTERS TO INCREASE FETAL-HEMOGLOBIN LEVELS

FIELD OF THE INVENTION

The present invention is directed to methods of increasing the level of fetal hemoglobin (HbF) in a subject in need of such treatment by administering to said subject one or more biologically active carboxylic acid compounds of Formulae (I–III) described herein below. In particular, this invention relates to preventing, treating or ameliorating β-globin or other HbF-related disorders by causing an increased production of fetal hemoglobin.

BACKGROUND OF THE INVENTION

Normal adult hemoglobin (HbA) is comprised of four polypeptide subunits, two α-globin chains and two β-globin chains. The α chains are encoded by a gene on chromosome 16, and the β chains are encoded by a gene on chromosome 11. During fetal life, fetal hemoglobin (HbF) is composed of four polypeptide subunits, similar to HbA. However, instead of two β-subunits, HbF contains two γ-subunits together with two α-subunits. Gamma-globin is also encoded on chromosome 11, upstream of β-globin.

The expression of the globin genes is regulated during ontogeny. The production of globin begins to switch from HbF, containing $\alpha 2 \gamma 72$, to HbA, containing $\alpha 2 \beta 2$, just before birth. The switching process to HbA is complete usually by 4 months after birth. However, some HbF continues to be produced in normal adults comprising about 1% of the total hemoglobin. As such, any structural or functional defects of the β-globin gene become clinically evident only on completion of the perinatal γ- to β-globin switch.

The β-hemoglobinopathies (globin disorders), such as sickle cell anemia and β-thalassemia (or Cooley's anemia), are among the most common of the genetic disorders, afflicting millions of people world-wide. They are incurable hereditary disorders of hemoglobin structure and synthesis, respectively, that have their origins in mutations affecting the β-globin gene locus or a region controlling its expression. In sickle cell anemia, a point mutation in the DNA sequence of the β-gene involving a replacement of glutamic acid with valine results in a defective β-globin protein which complexes with another of its kind forming polymerized proteins called hemoglobin S (HbS). The tendency towards sickling is dependent on both the relative quantity of HbS in erythrocytes and the level of oxygen tension in the micro environment of the body. These polymerized β-globins cause severe distortions in red cell morphology, membrane damage by blocking capillaries and lead to hemolysis and extreme, although episodic, pain. Other problems include liver involvement such as jaundice, hyperbilirubinemia, and severe anemia. No effective conventional therapies for sickle cell anemia exist and treatment of this disorder is confined to the management of acute pain and the consequences of end-organ damage.

β-thalassemia is characterized by inadequate or absent production of the β-globin chain which is the result of mutations in the gene or in the gene promotor. This results in an accumulation of excess α-globin chains, which are toxic to red cells and promote cell lysis. This premature destruction of red cells produces a severe anemia. To compensate for this, erythropoiesis expands dramatically resulting in hyperplastic marrow and consequently grossly enlarged bones. These patients require transfusions to sustain life, but the onset of iron overload results in death in most by the third decade of life. As yet, there is no effective conventional therapy for this disorder.

Several lines of evidence suggest that increasing cellular levels of HbF should prove clinically beneficial to sufferers of sickle cell anemia and β-thalassemia. A subpopulation of people with sickle cell anemia has been observed wherein these patients had unusually high levels (>10 to 100%) of HbF and displayed no clinical symptoms of the disorder. Further studies show that patients with slightly increased levels of HbF (above the normal 1%) have more mild or benign clinical symptoms. A level of 4–15% HbF approaches that considered necessary to ameliorate significantly the severity of sickle cell disease. Fetal hemoglobin has been found to decrease or inhibit polymerization of β-globin thus alleviating sickling of the red cells. Any increase in the production of non-α-globin in the case of β-thalassemia will result in more effective erythropoiesis thus ameliorating this disorder.

To date, several pharmacologic agents have shown a capacity for increasing the HbF synthesis in subjects. These include cell-cycle specific cytotoxic compounds, nucleoside analogues, hematopoietic growth factors and butyric acid derivatives. Cell-cycle specific compounds, such as 5-azacytidine, have resulted in increased levels of HbF. (Charache, S. et al. PNAS; 80:4842–4846, 1983). However these agents are carcinogenic and hence are unattractive as lifelong therapies, particularly for younger patients. Another drug that has been shown to increase HbF is the anti-cancer drug, hydroxyurea; however it also is toxic and not well tolerated by many patients. (Charache, S. et al., Blood; 69: 109–116, 1987.)

Perrine U.S. Pat. No. 4,822,821 (issued Apr. 18, 1989) provides a method for inhibiting the γ- to β-globin switching in fetal or infant subjects afflicted with β-globin disorders by administering α-amino-n-butyric acid or butyric acid and isomers thereof to the subject prior to the natural completion of the switching process. This patent does not describe the method of increasing HbF using compounds of the present invention or the administration of said compounds to adult subjects. The term "adult" as used herein and in the claims refers to subjects whose globin production has undergone the switch from γ-globin to β-globin; for human subjects, this switch normally takes place around 1–12 weeks after birth.

Perrine U.S. Pat. No. 5,025,029 (issued Jun. 18, 1991) provides a method for ameliorating β-globin disorders in a mammal comprising the step of introducing into the bloodstream of said mammal periodically during its gestation period and/or infancy a compound of the formula:

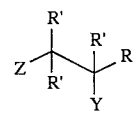

wherein

R is —CO$_2$R$_1$, —SO$_2$R$_1$, —SO$_3$R$_1$, or imidazole;

R' is NH$_2$, M, H, C$_1$–C$_4$, alkyl or perfluorinated alkyl;

M is a cation;

Z is —CH$_3$, X, or CX$_3$;

X is H, Cl, Br, I;

Y is H, —NH$_2$, —NH$^+_3$, —CX$_3$ or F; and

R' is H or F.

This patent does not describe the method using compounds of the present invention, or administration of said compounds to adult subjects.

While butyric acid and α-amino-n-butyric acid treatments have been shown to be quite effective at increasing HbF, these short chain fatty acids have relatively low potency and require prolonged and continuous treatment. These disadvantages make these compounds unattractive as a clinical therapies.

Still other butyrate compounds are presently being studied. Perrine and Faller (Experiencia, 49:133–137, 1993) have examined arginine butyrate. Dover, et. al., (New Eng. J. Med., 327:569–570, 1992) have shown that sodium phenyl acetate and it's prodrug sodium 4-phenylbutyrate are capable of increasing HbF in K562 leukemia cells. Fibach, E., et. al, (Blood, 82: 1–7, 1993) have shown that phenylacetate and 4-phenylbutyrate increase HbF in Erythroid precursor cells. However, all these compounds maintain many of the disadvantages of butyric acid, namely low intrinsic potency, a long induction period, a rapid metabolism and a high clearance. There remains the need for a therapeutic agent capable of enhancing HbF levels, but having a higher potency and low toxicity.

Recently, it has been shown that increasing the level of HbF in a subject is useful for the protection of malaria. HbF inhibits the maturation of the malaria parasites, hemosporidian, in erythrocytes. Perrine U.S. Pat. No. 5,216,004 (issued Jun. 1, 1993) provides a method of preventing malaria in a subject comprising the step of administering to said subject a compound of the formula:

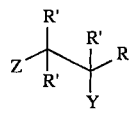

wherein

R is $-CO_2R_1$, $-SO_2R_1$, $-SO_3R_1$, or imidazole;

$R^1$ is $NH_2$, M, H, $C_1-C_4$, alkyl or perfluorinated alkyl;

M is a cation;

Z is X or $CX_3$;

X is H, Cl, Br, I;

Y is H, $-NH_2$, $-NH^+_3$, $-CX_3$ or F; and

R' is H or F, in an amount sufficient to inhibit development of malarial parasites. This reference does not teach the method of using compounds of the present invention to increase HbF.

Nudelman et al, U.S. Pat. No. 5,200,553 (issued Apr. 6, 1993) described carboxylic acid esters useful to promote antitumor or immune responses selected from the group consisting of compounds having the Formulae (I), (II), or (III):

(I) $XCH_2-CHX-CHX-C(=O)-O-Z$ (II) $CH_3-CO-CH_2-C(=O)-O-Z$ (III) $CH_3-CH_2-CO-C(=O)-O-Z$ wherein X is H, or one of X only may be OH; Z is $-CHR-O-(O=)C-R'$; R represents a member selected from the group consisting of H and alkyl; and R' represents a member of the group consisting of alkyl, aminoalkyl, aralkyl, aryl, alkoxy, aralkoxy and aryloxy, in which aryl by itself, and aryl in aralkyl, aralkoxy and aryloxy are each selected from the group consisting of sub-groups (a) and (b), wherein (a) is unsubstituted phenyl, naphthyl, furyl, or thienyl and (b) is phenyl, naphthyl, furyl, or thienyl, each of which is substituted by at least one substituent selected from the group consisting of alkyl, alkoxy, or halogen, provided that in (I) when X is H and R' is propyl, then R is alkyl which contains at least three carbon atoms.

None of the above references teach or suggest the method of using carboxylic acid compounds of Formulae (I–III) to increase the level of HbF in vitro, or in vivo in subjects and particularly in adult subjects. Accordingly, an object of the present invention is the method of increasing the level of HbF comprising administering one or more compounds of Formulae (I–III). It is a further object of this invention to provide a method for increasing HbF levels in adults in need of such treatment without toxicity and with greater potency. Still a further object of this invention is to provide a method of increasing HbF in vitro for diagnostic purposes comprising utilizing a compound of the Formulae (I–III). The methods of the present invention are particularly useful for preventing or ameliorating the clinical effects of various disorders by increasing the level of HbF in subjects afflicted with such anomalies. Such disorders include but are not limited to globin disorders (such as sickle cell anemia and β-thalassemia) and malaria.

SUMMARY OF THE INVENTION

The present invention provides a method of increasing the level of HbF comprising administering one or more compounds of Formulae (I), (II), or (III):

(I) $XCH_2-CHX-CHX-C(=O)-O-Z$ (II) $CH_3-CO-CH_2-C(=O)-O-Z$ (III) $CH_3-CH_2-CO-C(=O)-O-Z$ wherein:

X is H, or one of X only may be OH;

Z is $-CHR-O-C(=O)R'$, $-CHR-O-C(=O)-O-R'$, or

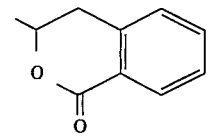

R is H, alkyl, aryl, arylalkyl; and

R' is alkyl, aminoalkyl, aralkyl, aryl, alkoxy, aralkoxy and aryloxy, in which aryl by itself, and aryl in aralkyl, aralkoxy and aryloxy are each selected from the group consisting of phenyl, naphthyl, furyl, or thienyl, each of which is unsubstituted or substituted by at least one substituent selected from the group consisting of alkyl, alkoxy, or halogen;

and pharmaceutically acceptable salts and prodrugs thereof.

In the compounds of Formulae (I–III) and in the pharmaceutical compositions which contain compounds defined with respect to Formulae (I–III), it is preferred that alkyl radicals, including those which form part of alkoxy, aralkyl and aralkoxy radicals contain no more than about 20 carbon atoms.

Preferred is the method of increasing HbF in a subject comprising administering a compound wherein R is hydrogen, methyl, ethyl, propyl, isopropyl, butyl, isobutyl, secondary butyl or tertiary butyl, and R' is methyl, ethyl, propyl, isopropyl, butyl, isobutyl, secondary butyl, tertiary butyl, methoxy, ethoxy, propoxy, isopropoxy, butoxy, isobutoxy, secondary butoxy or tertiary butoxy.

Specifically preferred is the method of increasing HbF in a subject comprising administering a compound selected from the group consisting of pivaloyloxymethyl butyrate; ethylidene dibutyrate; butylidene dibutyrate; (1-butyroxy) ethyl ethyl carbonate; 2,2-dimethylpropylidene dibutyrate; 3-(butyroxy)phthalide; (butyroxy)methyl octanoate; methylidene dibutyrate; ((2-methylpropanoyl)oxy)methyl butyrate; tocopheryl butyrate; and glyceryl tributyrate.

It is a further object of this invention to provide a method for increasing HbF levels in adults in need of such treatment without toxicity and with greater potency.

The present invention further provides a method of treating, preventing or ameliorating β-globin or other HbF-related disorders by increasing the level of HbF in subjects in need of such treatment comprising administering one or more biologically active compounds of Formulae (I–III). Preferred is the method of treating, preventing or ameliorating malaria or a β-globin disorder selected from the group consisting of sickle cell anemia and β-thalassemia.

While it is possible to utilize the compounds in vivo as a raw chemical, it is preferable to present them as a pharmaceutical composition.

The methods according to the present invention may also be utilized in vivo or in vitro for diagnostic purposed, such as in cell cultures taken from patients to determine the potential efficacy of further treatment for the various disorders.

DETAILED DESCRIPTION

The present invention provides a method for increasing HbF in a subject in need of such treatment comprising administering one or more compounds of Formulae (I), (II), or (III):

(I) $XCH_2—CHX—CHX—C(=O)—O—Z$
(II) $CH_3—CO—CH_2—C(=O)—O—Z$
(III) $CH_3—CH_2—CO—C(=O)—O—Z$ wherein:

X is H, or one of X only may be OH;

Z is —CHR—O—C(=O)R', —CHR—O—C(=O)—O—R', or

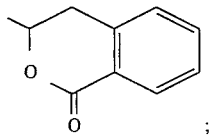

R is H, alkyl, aryl, arylalkyl; and

R' is alkyl, aminoalkyl, aralkyl, aryl, alkoxy, aralkoxy and aryloxy, in which aryl by itself, and aryl in aralkyl, aralkoxy and aryloxy are each selected from the group consisting of phenyl, naphthyl, furyl, or thienyl, each of which is unsubstituted or substituted by at least one substituent selected from the group consisting of alkyl, alkoxy, or halogen; and pharmaceutically acceptable salts and prodrugs thereof.

The compounds herein described may have asymmetric centers. All chiral, diastereomeric, and racemic forms are included in the present invention. Many geometric isomers of olefins and the like can also be present in the compounds described herein, and all such stable isomers are contemplated in the present invention.

When any variable (for example, R and R', etc.) occurs more than one time in any constituent or in Formulae (I–III) or any other formula herein, its definition on each occurrence is independent of its definition at every other occurrence. Also, combinations of substituents and/or variables are permissible only if such combinations result in stable compounds.

As used herein and in the claims, "alkyl" is intended to include both branched-, straight- or cyclic- saturated aliphatic hydrocarbon groups having the specified number of carbon atoms; as e.g. methyl, ethyl, propyl, isopropyl, butyl, isobutyl, secondary butyl, tertiary butyl, hexyl, cyclohexyl, heptyl, octyl, decyl, dodecyl or octadecyl. As used herein and in the claims, "aryl" or "aromatic residue" is intended to mean phenyl, furyl, thienyl or naphthyl; "carbocyclic" is intended to mean any stable 5- to 7-membered monocyclic or bicyclic or 7- to 14-membered bicyclic or tricyclic carbon ring, any of which may be saturated, partially unsaturated, or aromatic, for example, indanyl or tetrahydronaphthyl (tetralin). Aryl radicals, including those which form part of aralkyl, aryloxy and aralkoxy radicals, may be substituted or not, and may be carbocyclic; substituents when present may be selected from, e.g. alkyl, alkoxy and halogen. The term "alkoxy", as used herein and in the claims, represents an alkyl group of indicated number of carbon atoms attached through an oxygen bridge.

The term "substituted" as used herein and in the claims, means that one or more hydrogens on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein and in the claims, "therapeutically effective amount" refers to that amount necessary to administer to a host to achieve the desired result of increasing HbF, to prevent, treat or ameliorate β-globin or other HbF-related disorders.

As used herein and in the claims, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo in relation to the parent compounds. Examples include, but are not limited to, mineral or organic acid salts of basic residues such as amines; alkali or organic salts of acidic residues such as carboxylic acids; acetate, formate and benzoate derivatives of alcohols and amines; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference in its entirety.

The compounds of Formulae (I–III) provided by the present invention may be prepared generally by any method known in the art for formation of an ester group (when R' represents alkoxy, aralkoxy or aryloxy) or a carbonate group and is also described in U.S. Pat. No. 5,200,533 which is incorporated herein by reference in its entirety.

For example, compounds wherein R' is other than propyl may be prepared by reacting butyric acid with a reagent of formula Y—CHR—O—(O=)C—R' in presence of a base, where Y is leaving group such as halogen, methanesulfonate or P-toluenesulfonate, and R and R' are as previously defined. The base may be e.g. a trialkylamine, pyridine or an alkali metal carbonate. The reaction may be carried out in absence or in presence of an inert solvent. When a solvent is used, this may be, for example, acetone, ether, benzene, toluene, tetrahydrofuran, ethyl acetate, acetonitrile, dimethylformamide, dimethyl sulfoxide, chloroform, dioxane or 1,2-dichloroethane.

When R' is propyl, the compounds may be prepared by an alternate process by reacting butyric anhydride with an aldehyde of the formula (R—CHO), wherein R is as defined above, in presence of an acid catalyst such as boron trichloride, aluminum trichloride, tin dichloride, sulfuric acid, phosphoric acid or zinc chloride.

The compounds of Formulae (I–III) can be illustrated by the following non-limiting examples:

EXAMPLE 1

Pivaloyloxymethyl Butyrate $^1$H-NMR ppm (CDCl$_3$): 5.753 (s, 2H). 2.336 (t, 2H), 1.670 (sextet, 2H), 1.213 (s. 9H). 0.953 (t, 3H).

EXAMPLE 2

Ethylidene Dibutyrate $^1$H H-NMR ppm (CDCl$_3$); 6.88 (q. J=5.6 Hz, 1H), 2.30 dt, J=0.75, 7.5 Hz, 4H), 1.65 (sextet, J=7.5 Hz. 4H). 1.47 (d. J=5.5 Hz, 3H). 0.95 (t, J=7.5 Hz, 6H).

EXAMPLE 3

Butylidene Dibutyrate $^1$H-NMR ppm (CDCl$_3$): 65 6.82 (t, J=5.6 Hz, 1H), 2.30 (m, 4H), 1.75 (m, 2H). 1.65 (sextet, J=7.5 Hz, 4H), 1.40 (q, J=7.5 Hz, 2H). 0.953 and 0.949 (2t, J=7.5 Hz, 9H).

EXAMPLE 4

(1-Butyroxy)ethyl Ethyl Carbonate $^1$H-NMR ppm (CDCl$_3$): 6.77 (q. J=5 Hz, 1H), 4.22 (q. J=7 Hz, 2H), 2.32 (t, J=7.5 Hz, 2H), 1.66 (sextet, J=7.5 Hz, 2H), 1.52 (d, J=5.5 Hz, 3H), 1.318 (t, J=7.5 Hz, 3H), 0.95 (t, J=7.5 Hz, 3H).

EXAMPLE 5

2,2-Dimethylpropylidene Dibutyrate $^1$H-NMR ppm (CDCl$_3$): 6.59 (s, 1H), 2.31 (t, 1H), 2.20 (sextet, 4H), 1.50 (s, 9H), 1.49 (t, 6H).

EXAMPLE 6

Octanoyloxymethyl Butyrate $^1$H-NMR ppm (CDCl$_3$): 5.70 (s, 2H), 2.38–2.11 (m, 4H), 1.7–1.6 (m, 4H), 1.3–1.1 (m, 8H), 0.92 (t, 0.87 (t, 3H).

EXAMPLE 7

3-(Butyroyloxymethyl)phthalide $^1$H-NMR ppm (CDCl$_3$): 7.93 (dd, J=0.7, 7.5 Hz, 1H), 7.76 (dt, J=1.1, 7.5 Hz, 1H), 7.65 (dt, J=1.0, 8.2 Hz, 1H), 7.58 (dd, J=0.7, 8.2 Hz, 1H), 7.46 (s, 1H), 2.42 (t, J=7.4, Hz, 2H), 1.72 (sextet, J=7.4, Hz, 2H), 0.99 (t, J=7.4, Hz, 3H).

EXAMPLE 8

(5-Methyl-2-oxo-1,3-dioxalan-4-yl)methyl Butyrate $^1$H-NMR ppm (CDCl$_3$): 4.82 (s, 2H), 2.31 (t, 2H), 2.15 (s, 3H), 1.64 (sextet, 2H), 0.94 (t, 3H).

EXAMPLE 9

Iso-butyroyloxymethyl Butyrate $^1$H-NMR ppm (CDCl$_3$): 5.77 (s, 2H), 2.60 (septet, 1H), 2.36 (t, 2H), 1.69 (sextet, 2H), 1.19 (d, 6H), 0.96 (t, 3H).

These procedures outlined above can be improved by one skilled in the art by, for instance, changing the temperature or stoichiometry of the reactions. Any such changes are intended to fall within the scope of this invention.

UTILITY

The method of administering compounds of Formulae (I–III) are useful to increase the level of HbF in vivo or in vitro. For instance, said methods are useful as providing an in vitro diagnostic tool. Preferably, said methods are useful as providing therapeutic agents for the prevention, treatment or amelioration of various disorders by increasing the level of HbF in a mammal afflicted with such disorder. The method of increasing the level of HbF by administering one or more compounds of the present invention is demonstrated using standard assays for measuring HbF production, for example, the assay described below.

The level of HbF was measured using a standard in vitro assay described by Ginder, G. D. et. al., (PNAS; 81: 3954–3958, 1984) and Fibach, C. et. al., (Blood; 82:1–7, 1993), both of which are hereby incorporated by reference in their entireties. Said in vitro assay for measuring the ability of compounds to increase HbF is generally accepted as a valuable tool to predict in vivo patient response in the clinical setting (Fibach, C. et. al., Ginder, G. D. et. al., and Perrine, S. P.; In: Stamatoyannopoulos G. et. al., eds., The regulation of hemoglobin switching; Proceedings of the Seventh Conference on Hemoglobin Switching, Sep. 8–11, 1990; Johns Hopkins Unit Press 1991: 425–436.)

Erythroid Cell Cultures

PERIPHERAL BLOOD: This is a two-phase liquid Erythroid cell culture assay. Peripheral blood was obtained from normal donors or subjects having a β-globin disorder. Peripheral blood mononuclear cells were isolated by centrifugation on a gradient of Ficoll-Hypaque (Lymphocyte Separation Medium, Organon Teknika, Durham, N.C.) and cultured for 7 days (phase 1) in α-minimal essential medium supplemented with 10% fetal calf serum (FCS) (both from GIBCO, Grand Island, N.Y.), 1 µg cyclosporine A (Sandoz, Basel Switzerland) and 10% conditioned medium collected from bladder carcinoma 5637 cultures (ATCC, Rockville Md.). In phase II, the nonadherent cells were recultured in α-medium supplemented with 30% FCS, 1% deionized bovine serum albumin, 1×10–5M 2-mercaptoethanol, 1.5 mM glutamine, 1 µM dexamethasone (all from Sigma, St. Louis, Mo.) and 1 µ/ml human recombinant erythropoietin (Cilag Pharmaceuticals). Compounds were added on day 6; cultures were harvested on day 13.

MURINE ERYTHROLEUKEMIA CELLS (MELS): MELS were grown in RPMI media with 10% FCS, supplemented with 2mM glutamine. Cells were incubated at 37° C. in a humidified 5% CO$_2$ incubator. Viability was determined by trypan blue exclusion. MEL cells were exposed to butyric acid or a compound of Formulae (I–III); cultures were harvested four days following treatment.

Quantitation of Hb

Differentiation of erythroid cells was assessed morphologically by preparing cytocentrifuge slides stained with alkaline benzidine according to the procedure of Fibach et al., (1989) Blood 73:100–103, which is incorporated herein by reference in its entirety. The HbF-containing cells stain positively and the percent of HbF-containing cells was determined. Total Hb, HbF, and sickle-hemoglobin (HbS) were characterized and quantitated by cation exchange high pressure liquid chromatography as described in Perrine (Blood, 74:1963–1967, 1989) which is hereby incorporated by reference in its entirety. The mean cellular Hb concentration was calculated by dividing the Hb content by the number of benzidine-positive cells. The percent of HbF or HbS was determined from cells treated with compound and from untreated cells (base level).

The effect on the level of HbF in blood cultures by Butyric Acid (BA) was compared with the compound of Example 3 (a representative compound of the invention). The results of average percent increase of Hb from are presented in table 1.

TABLE 1

| Hb Produced by Erythroid Progenitor Cells | | |
|---|---|---|
| Concentration (µM) | Butyric Acid (%) | Example 3 (%) |
| 50 | 0.6 | 6.3 |
| 75 | 1.2 | 11.0 |
| 100 | 2.5 | 11.0 |
| 250 | 8.6 | 39.0 |
| 500 | 20.6 | 43.0 |

The results of table 1 show that the methods of using compounds of present invention produce an increase up to 43% in the percent Hb in cells from patients and this increase is greater than any increase seen by butyric acid.

Compounds of the present invention are also capable of causing a decreased level of HbS therefore inhibiting the expression of HbS in cells from sickle cell anemia patients, in addition to causing an increase of HbF. Methods to determine the amount of HbS and HbF are as described above.

Dosage and Formulation

The compounds of Formulae (I–III) can be administered for the method of increasing HbF by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice. The pharmaceutical compositions of the invention may be adapted for oral, parenteral, or rectal administration, and may be in unit dosage form, as is well known to those skilled in the pharmaceutical art.

In the pharmaceutical compositions of the invention, wherein the active ingredient has the Formulae (I–III) as defined herein, the preferences for R and R' set forth above also apply.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 3000 milligrams per kilogram of body weight, with the preferred dose being 100 to about 2000 mg/kg.

Dosage forms (compositions suitable for administration) contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid or semi-solid dosage forms, such as hard or soft-gelatin capsules, tablets, and powders, or in liquid dosage forms, such as elixirs, syrups, and suspensions. It can also be administered parenterally, in sterile liquid dosage forms. Other dosage forms are potentially possible such as administered transdermally, via a patch mechanism or ointment.

Gelatin capsules or liquid filled soft gelatin capsules contain the active ingredient and powdered or liquid carriers, such as lactose, lecithin starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), polysorbate and related sugar solutions and glycols such as propylene glycol or polyethylene glycols are suitable carriers for parenteral solutions. Solutions or emulsions for parenteral administration preferably contain about 5–15% polysorbate 80 or lecithin, suitable stabilizing agents, and if necessary, buffer substances. Antioxidizing agents, such as but not limited to sodium bisulfite, sodium sulfite, or ascorbic acid, either alone or combined, are suitable stabilizing agents. Also used could be citric acid and its salts and sodium EDTA. In addition, parenteral solutions can contain preservatives, such as but not limited to benzalkonium chloride, methyl- or propyl-paraben, and chlorobutanol.

Suitable pharmaceutical carriers are described in *Remington's Pharmaceutical Sciences,* Mack Publishing Company, a standard reference text in this field, which is incorporated herein by reference in its entirety.

Useful pharmaceutical dosage-forms for administration of the compounds of this invention can be illustrated as follows:

Capsules

A large number of unit capsules are prepared by filling standard two-piece hard gelatin capsules each with 10–500 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, lecithin, cottonseed oil or olive oil is prepared and injected by means of a positive displacement pump into gelatin to form soft gelatin capsules containing 10–500 milligrams of the active ingredient. The capsules are washed and dried.

Tablets

A large number of tablets are prepared by conventional procedures so that the dosage unit was 10–500 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Various modifications of the invention in additions to those shown and described herein will be apparent to those skilled in the art from the foregoing description. Such modifications are also intended to fall within the scope of the appended claims.

The foregoing disclosure includes all the information deemed essential to enable those skilled in the are to practice the claimed invention. Because the cited patents or publications may provide further useful information these cited materials are hereby incorporated by reference in their entirety.

What is claimed is:

1. A method of increasing the level of HbF in a subject comprising administering one or more compounds of the Formulae (I), (II), or (III):

(I) XCH$_2$—CHX—CHX—C(=O)—O—Z (II) CH$_3$—CO—CH$_2$—C(=O)—O—Z (III) CH$_3$—CH$_2$—CO—C(=O)—O—Z wherein:

X is H, or one of X only may be OH;

Z is —CHR—O—C(=O)R' or —CHR—O—C(=O)—O—R';

R is H, alkyl, aryl, arylalkyl; and

R' is alkyl, aminoalkyl, aralkyl, aryl, alkoxy, aralkoxy and aryloxy, in which aryl by itself, and aryl in aralkyl, aralkoxy and aryloxy are each selected from the group consisting of phenyl or naphthyl each of which is unsubstituted or substituted by at least one substituent selected from the group consisting of alkyl, alkoxy, or halogen; and pharmaceutically acceptable salts and prodrugs thereof.

2. The method of claim 1 comprising administering a compound of Formulae (I–III) wherein:

R is hydrogen, methyl, ethyl, propyl, isopropyl, butyl, isobutyl, secondary butyl or tertiary butyl, and R' is methyl, ethyl, propyl, isopropyl, butyl, isobutyl, secondary butyl, tertiary butyl, methoxy, ethoxy, propoxy, isopropoxy, butoxy, isobutoxy, secondary butoxy or tertiary butoxy.

3. The method of claim 1 comprising administering a compound selected from the group consisting of pivaloyloxymethyl butyrate; ethylidene dibutyrate; butylidene dibutyrate; (1-butyroxy)ethyl ethyl carbonate; 2,2-dimethylpropylidene dibutyrate; (butyroxy)methyl octanoate; methylidene dibutyrate; ((2-methylpropanoyl)oxy)methyl butyrate; and glyceryl tributyrate.

4. The method of claim 1 comprising administering the compound ethylidene dibutyrate.

5. The method of claim 1 comprising administering the compound butylidene dibutyrate.

6. The method of claim 1 comprising administering the compound (1-butyroxy)ethyl ethyl carbonate.

7. The method of claim 1 comprising administering the compound (butyroxy)methyl octanoate.

8. A method of treating, preventing or ameliorating β-globin or other HbF-related disorders by increasing the level of HbF in a subject in need of such treatment comprising administering one or more compounds of the Formulae (I), (II), or (III):

(I) XCH$_2$—CHX—CHX—C(=O)—O—Z (II) CH$_3$—CO—CH$_2$—C(=O)—O—Z (III) CH$_3$—CH$_2$—CO—C(=O)—O—Z wherein:

X is H, or one of X only may be OH;

Z is —CHR—O—C(=O)R' or —CHR—O—C(=O)—O—R';

R is H, alkyl, aryl, arylalkyl; and

R' is alkyl, aminoalkyl, aralkyl, aryl, alkoxy, aralkoxy and aryloxy, in which aryl by itself, and aryl in aralkyl, aralkoxy and aryloxy are each selected from the group consisting of phenyl or naphthyl each of which is unsubstituted or substituted by at least one substituent selected from the group consisting of alkyl, alkoxy, or halogen; and pharmaceutically acceptable salts and prodrugs thereof.

9. The method of claim 8 comprising administering a compound of Formulae (I–III) wherein:

R is hydrogen, methyl, ethyl, propyl, isopropyl, butyl, isobutyl, secondary butyl or tertiary butyl, and R' is methyl, ethyl, propyl, isopropyl, butyl, isobutyl, secondary butyl, tertiary butyl, methoxy, ethoxy, propoxy, isopropoxy, butoxy, isobutoxy, secondary butoxy or tertiary butoxy.

10. The method of claim 8 comprising administering a compound selected from the group consisting of pivaloyloxymethyl butyrate; ethylidene dibutyrate; butylidene dibutyrate; (1-butyroxy) ethyl ethyl carbonate; 2,2-dimethylpropylidene dibutyrate; (butyroxy) phthalide; (butyroxy) methyl octanoate; methylidene dibutyrate; ((2-methylpropanoyl) oxy)methyl butyrate; and glyceryl tributyrate.

11. The method of claim 8 comprising administering the compound ethylidene dibutyrate.

12. The method of claim 8 comprising administering the compound butylidene dibutyrate.

13. The method of claim 8 comprising administering the compound (1-butyroxy)ethyl ethyl carbonate.

14. The method of claim 8 comprising administering the compound (butyroxy)methyl octanoate.

15. The method of any of claims 8 through 14 wherein the disorder is selected from the group consisting of sickle cell anemia, β-thalassemia and malaria.

16. A method of increasing the level of HbF in vitro for diagnostic purposes comprising administering one or more compounds of the Formulae (I), (II), or (III):

(I) XCH$_2$—CHX—CHX—C(=O)—O—Z (II) CH$_3$—CO—CH$_2$—C(=O)—O—Z (III) CH$_3$—CH$_2$—CO—C(=O)—O—Z wherein:

X is H, or one of X only may be OH;

Z is —CHR—O—C(=O)R' or —CHR—O—C(=O)—O—R';

R is H, alkyl, aryl, arylalkyl; and

R' is alkyl, aminoalkyl, aralkyl, aryl, alkoxy, aralkoxy and aryloxy, in which aryl by itself, and aryl in aralkyl, aralkoxy and aryloxy are each selected from the group consisting of phenyl or naphthyl each of which is unsubstituted or substituted by at least one substituent selected from the group consisting of alkyl, alkoxy, or halogen; and pharmaceutically acceptable salts and prodrugs thereof.

17. The method of claim 16 comprising administering a compound of Formulae (I–III) wherein:

R is hydrogen, methyl, ethyl, propyl, isopropyl, butyl, isobutyl, secondary butyl or tertiary butyl, and R' is methyl, ethyl, propyl, isopropyl, butyl, isobutyl, secondary butyl, tertiary butyl, methoxy, ethoxy, propoxy, isopropoxy, butoxy, isobutoxy, secondary butoxy or tertiary butoxy.

18. The method of claim 16 comprising administering a compound selected from the group consisting of pivaloyloxymethyl butyrate; ethylidene dibutyrate; butylidene dibutyrate; (1-butyroxy)ethyl ethyl carbonate; 2,2-dimethylpropylidene dibutyrate; (butyroxy)methyl octanoate; methylidene dibutyrate; ((2-methylpropanoyl)oxy)methyl butyrate; and glyceryl tributyrate.

19. The method of claim 15 comprising administering the compound ethylidene dibutyrate.

20. The method of claim 16 comprising administering the compound butylidene dibutyrate.

21. The method of claim 16 comprising administering the compound (1-butyroxy) ethyl ethyl carbonate.

22. The method of claim 16 comprising administering the compound (butyroxy)methyl octanoate.

* * * * *